United States Patent [19]
Augustine

[11] Patent Number: 5,961,480
[45] Date of Patent: Oct. 5, 1999

[54] WOUND COVERING

[75] Inventor: Scott Augustine, Bloomington, Minn.

[73] Assignee: Augustine Medical, Inc., Eden Prairie, Minn.

[21] Appl. No.: 09/272,181

[22] Filed: Mar. 18, 1999

Related U.S. Application Data

[62] Division of application No. 08/999,353, Dec. 29, 1997.

[51] Int. Cl.$^6$ ....................................................... A61F 5/00
[52] U.S. Cl. .................................. 602/41; 602/2; 602/14; 602/54; 607/108
[58] Field of Search .................................. 602/41–59, 2, 602/14, 79; 128/889; 607/96, 108, 99, 114; 126/204

[56] References Cited

U.S. PATENT DOCUMENTS

| | | |
|---|---|---|
| 222,690 | 12/1879 | Goldschmidt . |
| 697,637 | 4/1902 | Lee . |
| 720,812 | 2/1903 | Johnson . |
| 1,384,467 | 7/1921 | Homan . |
| 1,399,095 | 12/1921 | Webb, Sr. . |
| 1,777,982 | 10/1930 | Popp . |

FOREIGN PATENT DOCUMENTS

| | | |
|---|---|---|
| 0424165 A1 | 10/1990 | European Pat. Off. . |
| 0485657 | 5/1992 | European Pat. Off. . |
| 0607472 | 1/1993 | European Pat. Off. . |
| 1303238 | 9/1961 | France . |
| 1489127 | 7/1967 | France . |
| 1527887 | 4/1968 | France . |
| 2544202 | 10/1984 | France . |
| 3102674 | 9/1982 | Germany . |
| 3118232 | 11/1982 | Germany . |
| 3539533 | 5/1987 | Germany . |
| 269938 | 7/1950 | Switzerland . |
| 378465 | 7/1964 | Switzerland . |
| 89041158 | 5/1989 | WIPO . |
| 9400090 | 1/1994 | WIPO . |
| 9615745 | 5/1996 | WIPO . |

Primary Examiner—Richard J. Apley
Assistant Examiner—Kim M. Lee
Attorney, Agent, or Firm—Gray Cary Ware Freidenrich

[57] ABSTRACT

A non-contact wound covering for covering a wound. A peripheral sealing ring is covered by a barrier layer and this assembly is attached to the skin with an adhesive. The barrier layer and peripheral sealing ring together define a treatment volume over the wound. The barrier layer may include active and passive heaters and the sealing ring may dispense water to control the humidity of the treatment volume. One form of active heat is the transfer of a heated fluid to the wound covering.

9 Claims, 16 Drawing Sheets

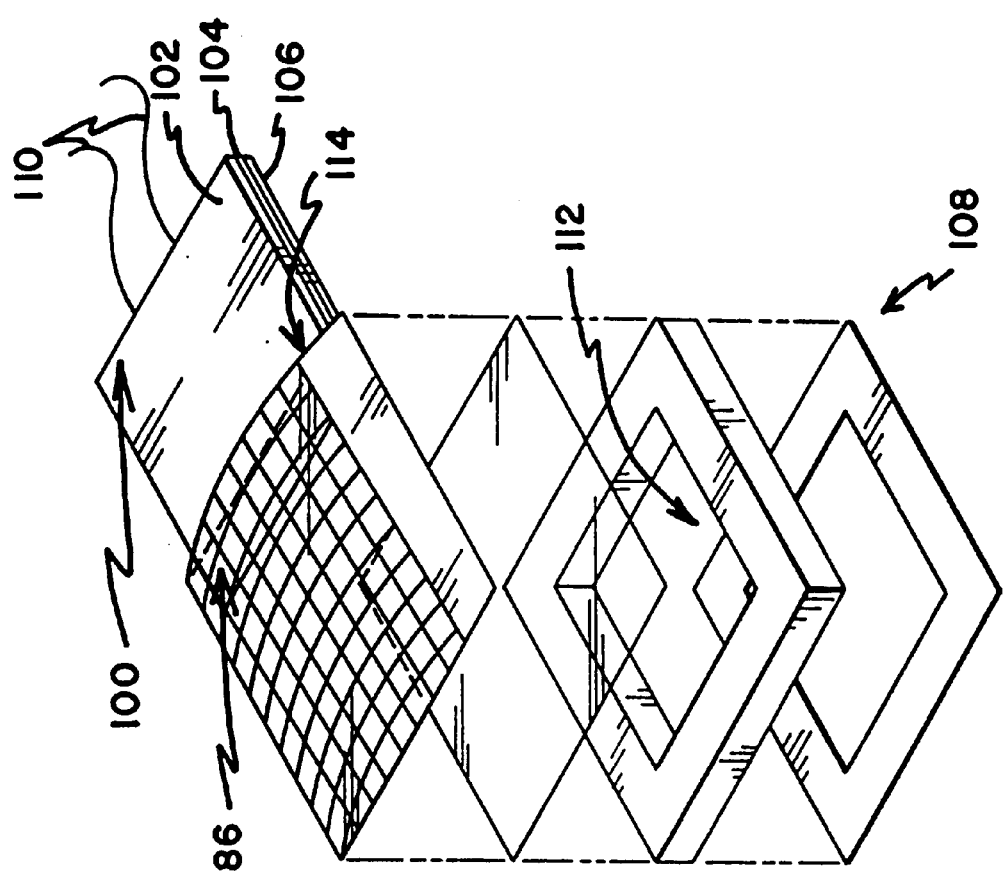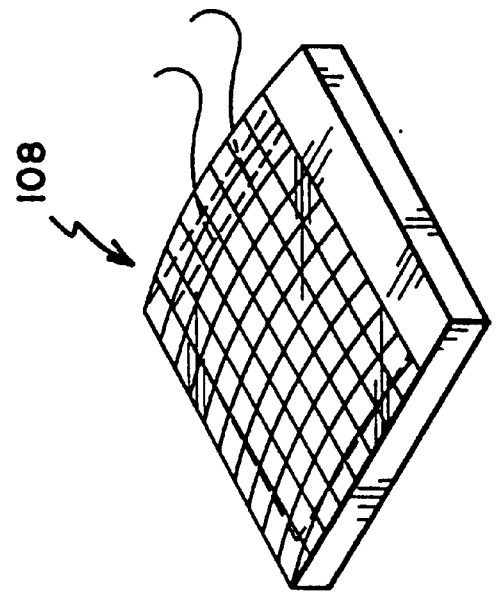

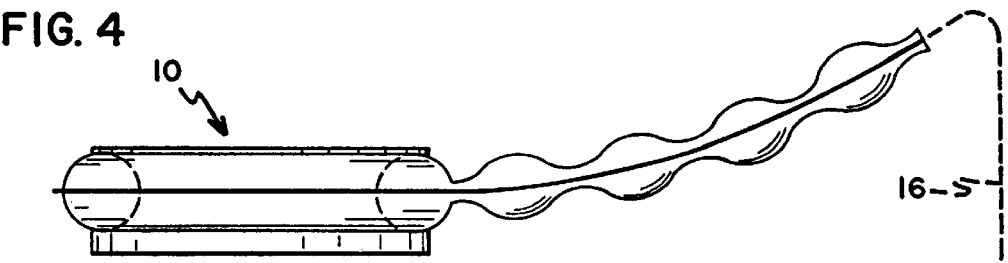
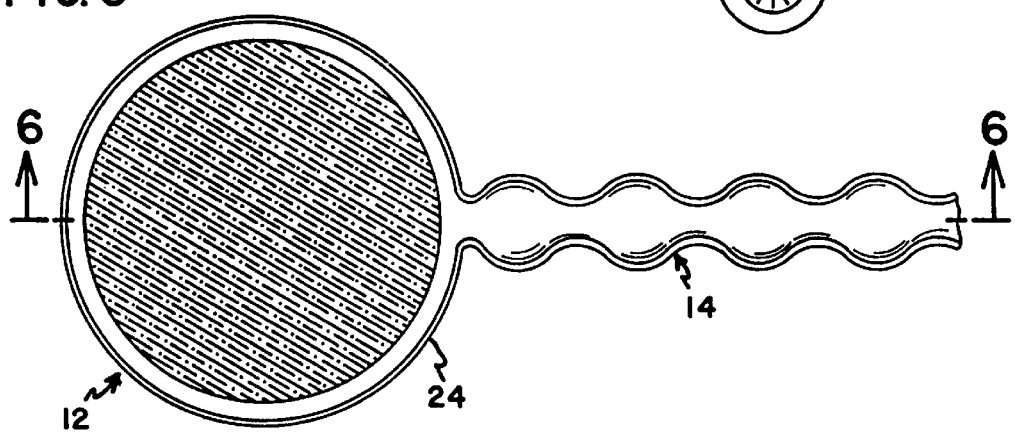
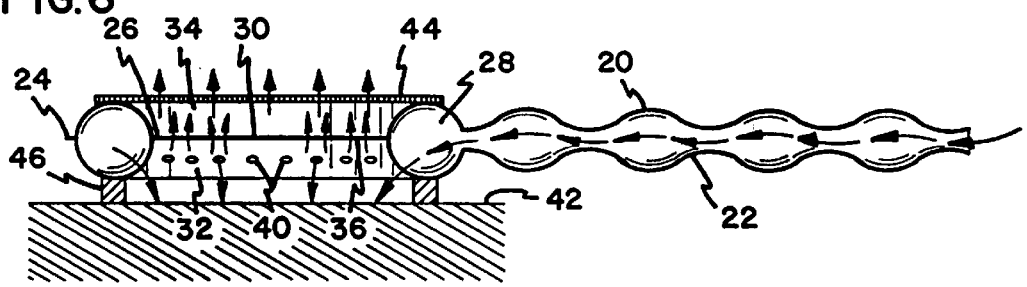
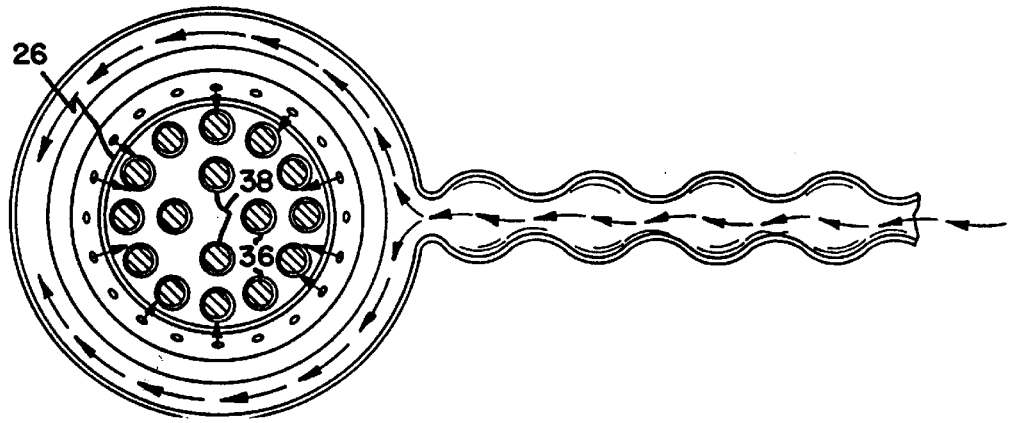

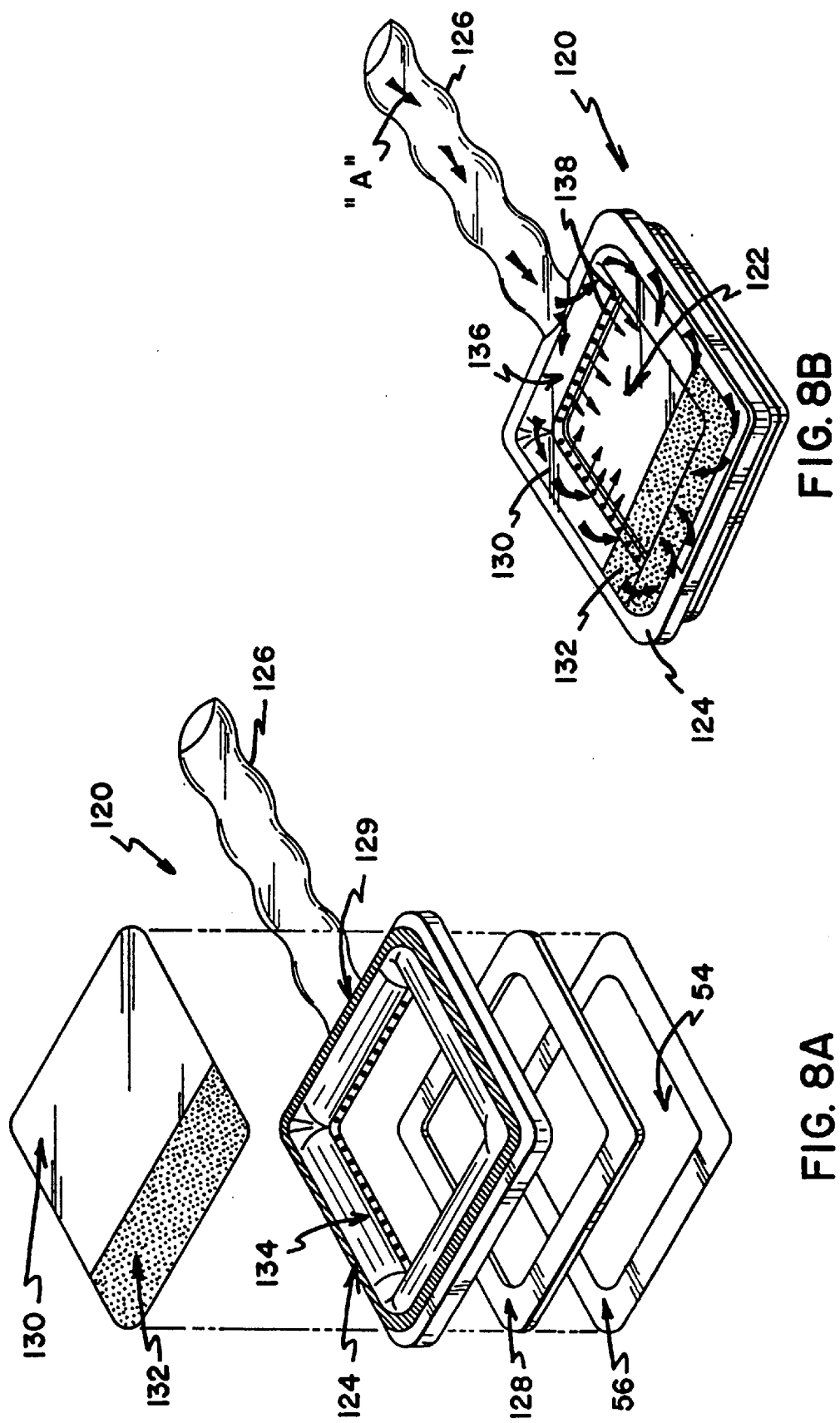

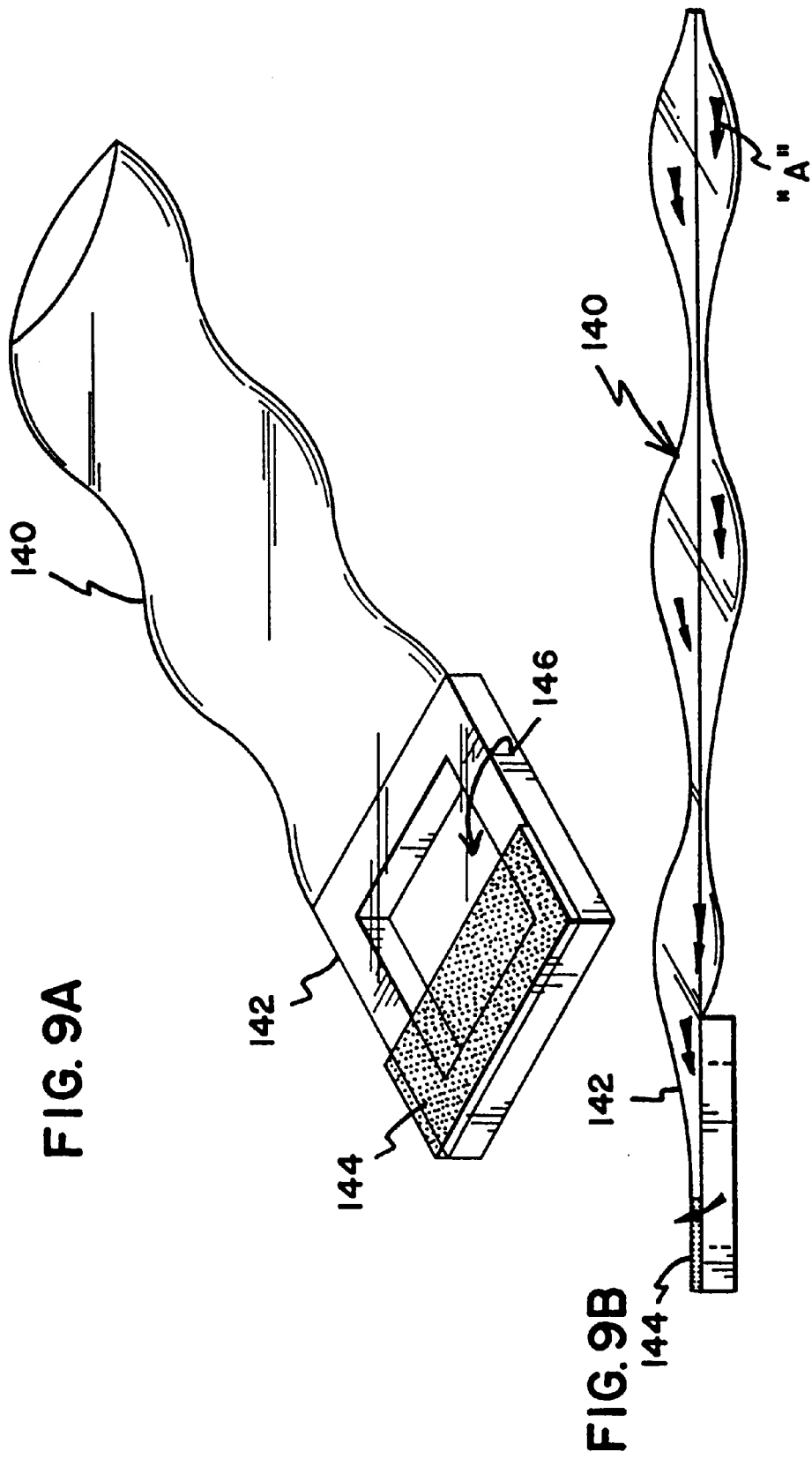

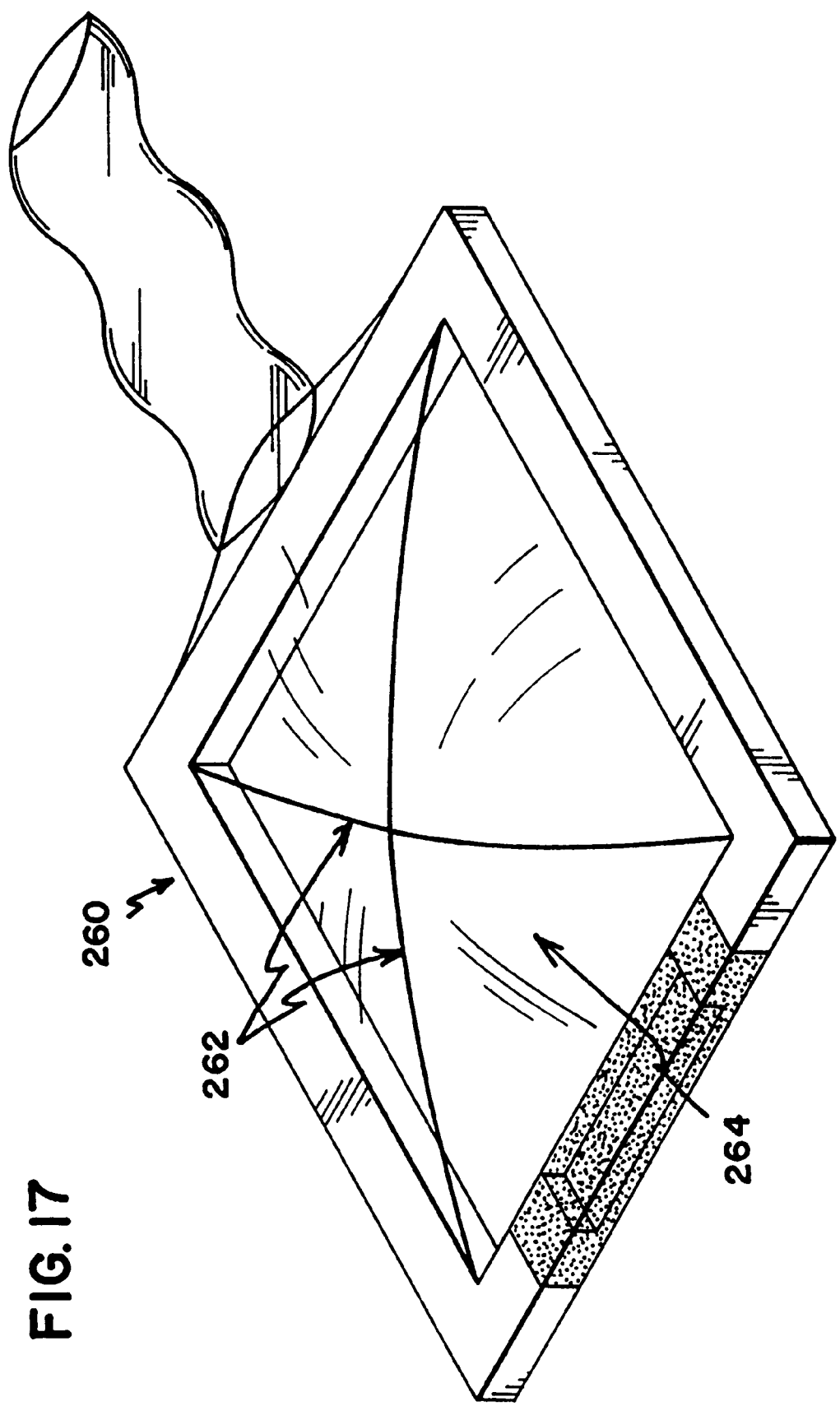

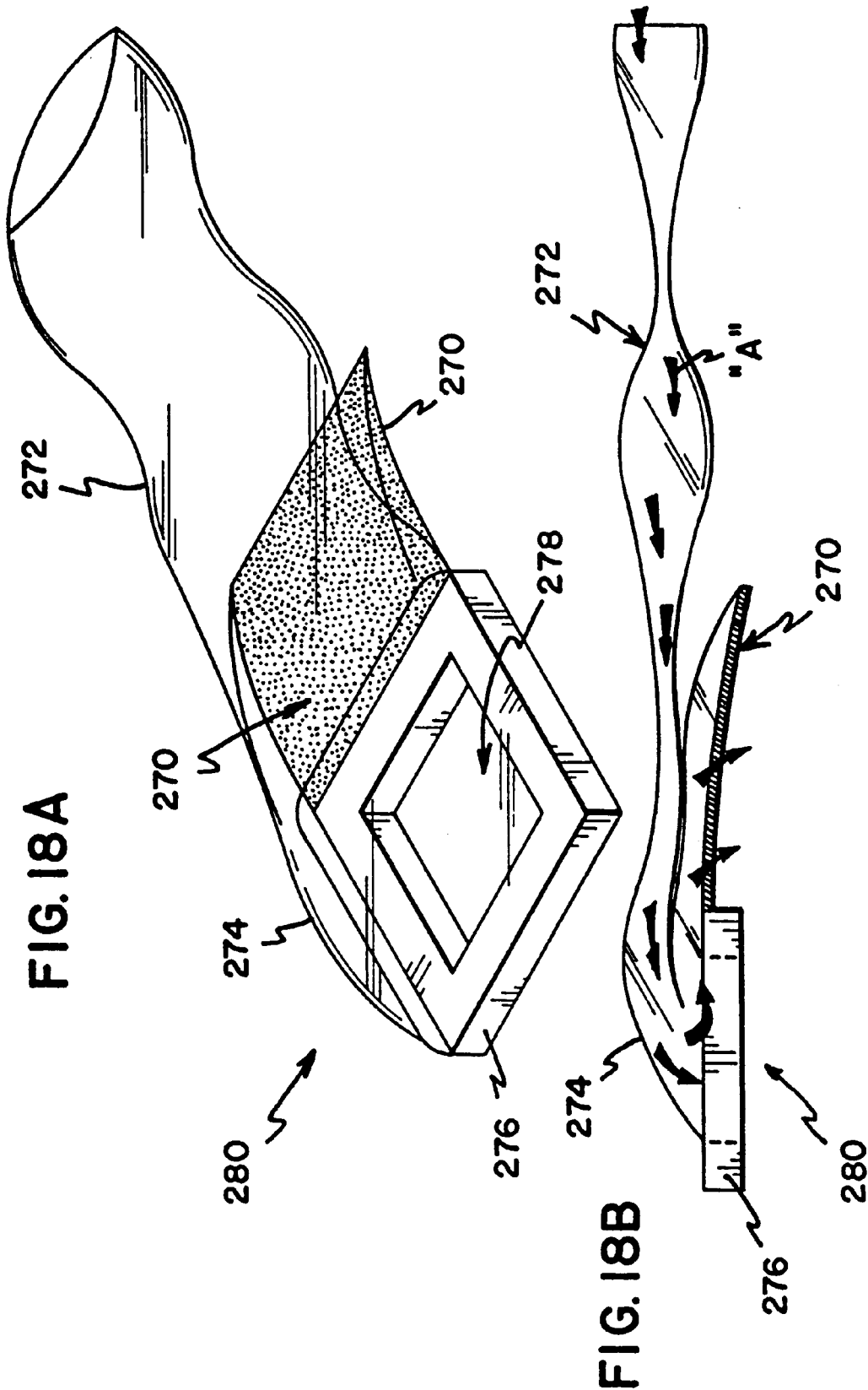

:::: {.columns}
::: {.column}
WOUND COVERING

This application is a divisional of patent application Ser. No. 08/999,353, filed Dec. 29, 1997.

BACKGROUND OF THE INVENTION

1. Field of the Invention

This invention relates to a wound covering for wound treatment. The wound covering overlays the wound area without touching the wound itself. The wound covering preferably controls the temperature, humidity and other aspects of the environment at the wound site.

2. Technical Background

Traditional wound coverings such as bandages are used to mechanically close wounds. Such bandages typically cover and touch the wound. Bandage contact with the wound and can interfere with the healing process.

The benefits of application of heat to a wound are known and documented benefits include: increased cutaneous and subcutaneous blood flow; increased partial pressure of oxygen at the wound site; increased immune system functions, including increased migration of white blood cells to the site.

However, in modern times, heat therapy for the. treatment of wounds and infection has been difficult to achieve in practice. Additionally the availability of antibiotics have taken precedence over other therapies for the treatment of wounds and topical infections.

The benefits of controlling other environmental parameters around the wound site are not as well known. Controlling the humidity at the wound site as well as the benefits of isolating the wound have not been extensively studied and documented.

SUMMARY OF THE INVENTION

The preferred form of the wound covering includes a peripheral sealing ring which, in use, completely surrounds the area of the wound. The upper surface of the peripheral sealing ring is spanned by a continuous barrier layer which is preferably transparent and substantially impermeable. An adhesive and a suitable release liner is applied to the lower surface of the peripheral sealing ring to facilitate the application of the wound covering to the patient's skin. Once in position, the sealing ring and the barrier layer define a wound treatment volume which surrounds the wound.

In accordance with actively heated embodiments of the invention, the barrier layer may include a pocket adapted to receive an active heater. An alternate form of the invention provides for the transport of heated air from a remote source, to the wound treatment volume. In the active heater embodiments a thermostat and/or a pressure activated switch may be used to control the heating effects of the electrically powered heater. Passively heated embodiments are contemplated as well. These passive versions of the device include the use of thermally insulating coverings which retain body heat within the treatment volume. These reflectors or insulators may be placed in a pocket formed in the barrier layer. Each of these heated embodiments promote wound healing by maintaining the wound site at a generally elevated but controlled temperature.

In general the peripheral sealing ring is made from an absorbent material which may acts as a reservoir to retain and dispense moisture into the treatment volume increasing the humidity at the wound site. The reservoir may also contain and deliver drugs and the like to promote healing.
:::
::: {.column}
BRIEF DESCRIPTION OF THE DRAWINGS Illustrative but not limiting embodiments of the invention are shown in the attached drawings. Throughout the several figures like reference numerals refer to identical structure throughout, in which:

FIG. 3A is an exploded view of an alternate wound covering;

FIG. 3B is an assembly view of the wound covering of FIG. 3A;

FIG. 4 is a side elevation view of a wound covering;

FIG. 5 is an enlarged top plan view of a wound covering;

FIG. 6 is an enlarged sectional view taken along line A—A of FIG. 5;

FIG. 7 is a bottom view of the wound covering of FIG. 4;

FIG. 8A is an exploded view of an alternate wound covering:

FIG. 8B is an assembly view showing the air flow through the wound covering;

FIG. 9A is a perspective view of an alternate wound covering;

FIG. 9B is a side view of the wound covering of FIG. 9A;

FIG. 17 is an alternate wound covering;

FIG. 18A is an alternate wound covering;

FIG. 18B is a side sectional view of the wound covering of FIG. 18A; and

DETAILED DESCRIPTION OF THE PREFERRED EMBODIMENTS

The present invention is directed to a non-contact wound covering for controlling the local environment at a wound site on a patient. The wound covering protects the wound from contamination by materials from the outside environment and also prevents the wound from site from sheading contaminants into the local environment of the patient, i.e.
:::
::::

the hospital room. The treatment volume formed over the wound site can be controlled to create an optimal healing environment. The word "wound" as used herein refers generically to surgical incisions, ulcers, or other lesions or breaks in the skin.

Each embodiment of the wound covering includes three basic element. First a vertical wall is provided to encircle the wound area on the surface of the patient's skin. This vertical structure is self supporting and provides an upper surface to support a barrier layer above the level of the wound. This structure is referred to throughout as the peripheral sealing ring. The next element is a barrier layer which is attached to the peripheral sealing ring. Together these elements form an enclosure or wound treatment volume over the wound site. The fact the barrier layer does not contact the wound itself promotes healing by minimizing mechanical stresses on the tissues. The barrier layer spans the entire wound area and attaches to the peripheral sealing ring. The third element is an adhesive and a complimentary release liner assembly which is attached to the lower surface of the sealing ring to facilitate attachment of the wound covering to the skin of the patient. As will be discussed in the various examples and illustrations detailed below, the three basic components of the wound covering are combined with other elements to provide an optimal healing environment at the wound site.

In accordance with the invention the climate within the wound treatment volume may be controlled. Typically the temperature, humidity, and gas composition is controlled. Also aerosolized medications or compounds can be released into this volume as well. The above list is exemplary of the climate controls which may promote healing of the wound, and is not intended to limit the scope of the present invention. It will be understood by those skilled in the art that numerous other climate factors can be controlled within the treatment volume of the present wound covering system without departing from the scope of the invention.

Figure 1A:
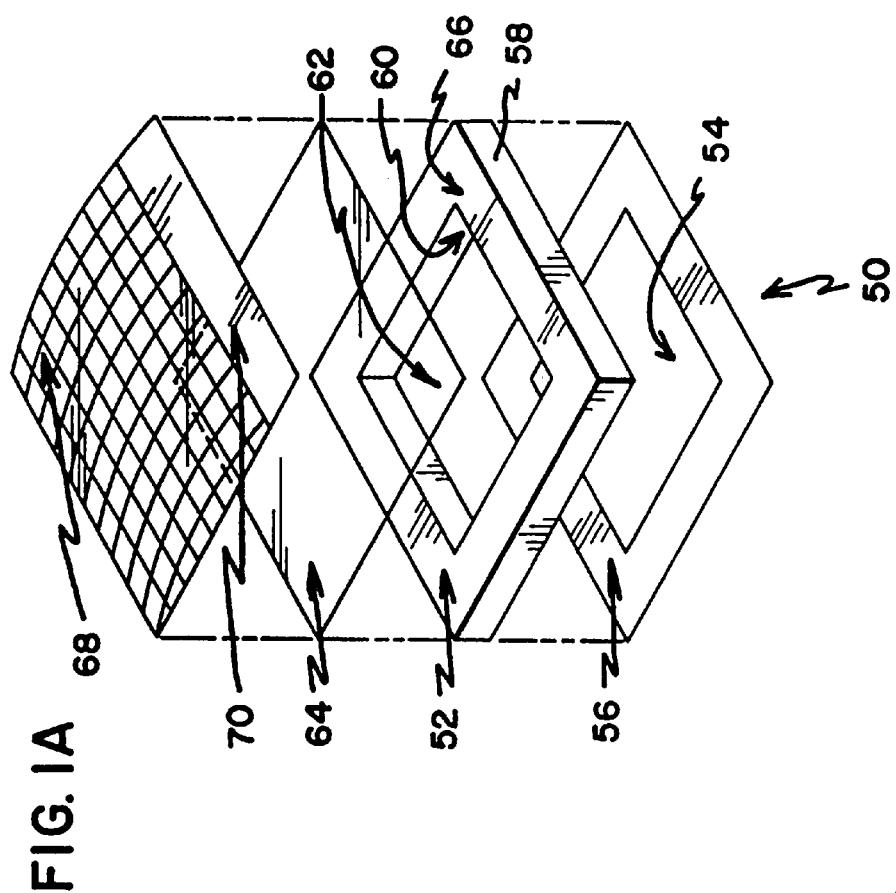
FIG. 1A is an exploded view of the wound covering.

FIG. 1A illustrates an exploded view of the wound covering 50. In this embodiment the peripheral sealing ring 52 is substantially square in outline. The peripheral sealing ring 52 is intended to be attached to uninjured skin surrounding the wound area 54 using an adhesive 56. In this embodiment a layer of adhesive hydrogel is shown as the adhesive 56. In this embodiment the peripheral sealing ring 52 is preferably constructed of an open cell hydrophilic foam plastic having a sealed outer surface 58 which isolates the wound from the environment. The peripheral sealing ring is fabricated from a material which is stiff but which may conform to the curved surface of the patient's body. The inner surface 60 of the sealing ring 52 is preferably porous or absorbent so that it can form a reservoir to contain and release moisture or water vapor into the air within the treatment volume 62 to create a high humidity environment if desired. Additionally, the hydrophilic absorbent nature of the peripheral sealing ring 52 absorbs fluids and blood weeping from the wound.

A barrier layer 64 is preferably attached to the upper surface 66 of the peripheral sealing ring 52 to seal the treatment volume 62. The barrier layer 64 is preferably constructed of a clear flexible plastic film, such as polyethylene or polyvinylchloride. In this embodiment a wound tracing grid 68, also constructed of a clear flexible material, may optionally be attached to the barrier layer 64 so that the physician can draw the wound as an aid to track the healing process of the wound. The wound tracing grid preferably contains a labeling area 70 for identifying the patient, date when the wound was traced, and other patient medical data.

It will be understood by those skilled in the art that the volume of the peripheral sealing ring 52 will depend on the structural strength of the support material and the amount of fluid absorption desired. Additionally, the total area of the peripheral sealing ring 52 is dependent on the size of the wound. For example, larger wounds and more flexible covers will require a thicker sealing ring so that the center of the cover does not touch the wound.

The upper surface 66 of the peripheral sealing ring 52 is preferably sealed by extending the barrier layer 64 over the entire upper surface 66 as seen in the drawing. The adhesive 56 for attaching the peripheral sealing ring 52 to the wound area 54 may take any form however the preferred adhesive is a preferably a two-faced hydrogel which attaches to the lower surface 72 of the peripheral sealing ring 52. This adhesive 56 permits the attachment of the peripheral sealing ring 52 to the patient's skin. Finally, the peripheral sealing ring 52 may serve as a reservoir for retaining water or medicaments in the treatment volume 62 in order to maintain a high humidity in the air within the volume. Water may be added to the peripheral sealing ring 52 at any time during treatment.

It will be understood by those skilled in the art that the peripheral sealing ring 52 can be supplied in a variety of shapes and sizes to accommodate various wounds. The shapes may include circles, squares, or rectangles. Although it is preferred to dispense the wound covering as a unitary assembly it should be apparent that individual segments of peripheral ring material could be assembled into any shape necessary to form a perimeter around the wound area. Likewise, the barrier layer 64 and wound tracing grid 68 could be provided in large sheets which may be cut to size and then attached to the peripheral sealing ring.

Figure 1B:
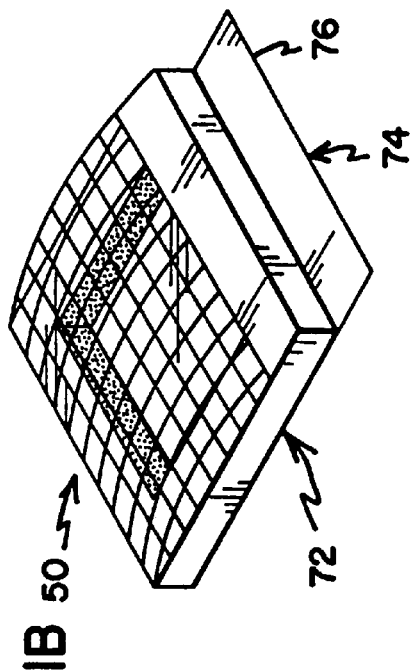
FIG. 1B illustrates an assembled view of the wound covering of FIG. 1A.

FIG. 1B is an assembled view of the wound covering 50 of FIG. 1A. To dispense the assembled product a release liner 74 is applied to the adhesive 56. The release liner may span the entire lower surface of the covering to maintains the sterility of the treatment volume 62. The release liner 74 preferably has a grip tab 76 to facilitate removal of the liner 74 from the wound covering 50 immediately prior to application of the wound covering 50 to the patient.

Figures 2A, 2B:
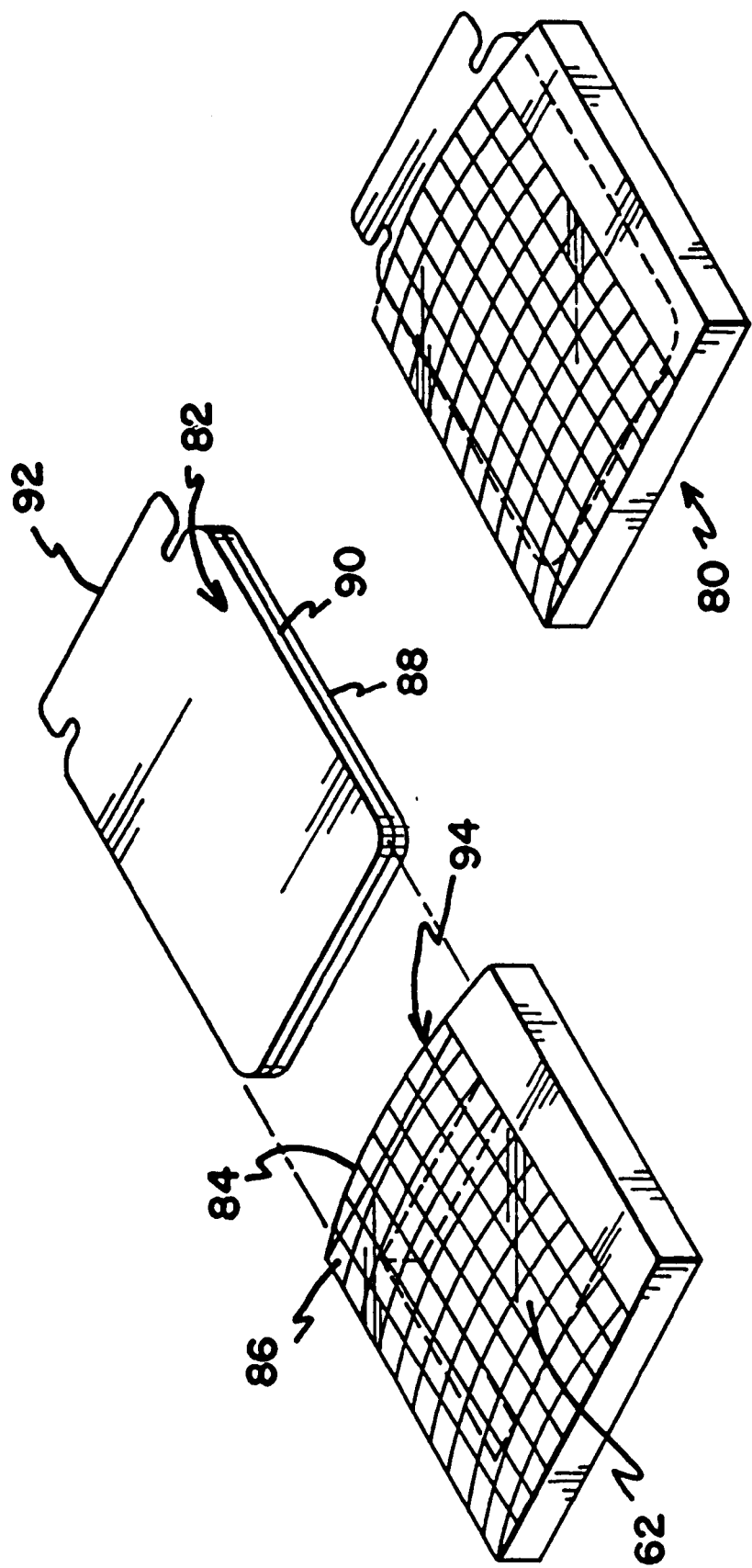
FIGS. 2A and 2B is a view of an alternate wound covering.

FIGS. 2A and 2B illustrate an alternate embodiment of the wound covering 80 utilizing passive heating of the treatment volume 62. Because heat is constantly being radiated from the body surface, the insulation properties of the trapped air within the treatment volume 62 will reduce this heat loss. By adding an infrared reflector 82 over the treatment volume 62, the infrared heat from the body can be reflected back to the skin for added passive heating.

One edge 84 of the wound tracing grid 86 is preferably not attached to the barrier layer to form an envelope or pocket 94 between the wound tracing grid 86 and the barrier layer. A piece of reflective foil material 88 may be inserted into the pocket 94. A thin layer of insulating material 90 may optionally be attached to the foil layer 88 to enhance heat retention and to provide the foil layer 88 with additional resiliency. A tab 92 is preferably attached to the infrared reflector 82 to allow easy insertion and removal from the pocket 94 and the wound covering 80.

FIGS. 3A and 3B illustrate an alternate embodiment of a non-contact wound covering 108 utilizing active heating of the treatment volume 112. Small to medium sized wounds (up to approximately six inches in diameter) may be safely and easily heated utilizing the foil heater assembly 100. The heater assembly 100 preferably comprises a pressure-sensitive switch 102, an insulating layer 104, and a foil heater element 106.

The pressure-sensitive switch 102 is preferably laminated to the upper layer of the heater assembly 100. The purpose of the switch 102 is to shut off power to the heater element 106 in the event that external pressure is applied to the wound covering 108 with sufficient force to cause the heater element 106 to contact the skin or wound below. This is an important feature to prevent the possibility of applying heat and pressure to the skin at the same time. The combination of heat and pressure is known to cause burns even at low temperatures (40° C.) because the pressure prevents blood flow in the skin making it susceptible to thermal injury. The pressure-sensitive switch 102 preferably covers the whole heater assembly 100 so that pressure applied anywhere to the surface of the heater assembly 100 will deactivate the heater element 106.

It will be understood that a variety of devices are suitable for use as the pressure-sensitive switch 102. For example, force sensing resistors resemble a membrane switch which changes resistance inversely with applied force. Devices of this type offer the substantial advantage of being low cost, flexible, and durable. It will be understood by those skilled in the art that a variety of other force sensing switch devices may be utilized as well.

The heater element 106 is preferably a thin film type resistance heater which is commercially available. Such thin film resistance heaters utilize low voltage, minimizing the electrical risk to the patient and allowing for battery-powered mobility. The heater element 106 is preferably sized for each wound covering 108. In actual use, the foil heater element 106 is preferably provided in large sheets with a pair of electrical leads 110 along one edge.

The foil heater assembly 100 is preferably inserted into a pocket 114 formed between the wound tracing grid 86 and the barrier layer as discussed above. Finally, a temperature monitoring device, such as a liquid crystal temperature monitor, may be applied to an upper surface of the foil heater assembly 100 or within the treatment volume 112 to monitor the temperature within the treatment volume 112.

FIG. 4 and FIG. 5, illustrate an alternate embodiment of the wound covering 10. In this embodiment the wound covering 10, includes a generally circular head, designated generally at 12, which transitions to an elongated non-kinking, collapsible air supply or hose 14.

The apparatus, as illustrated in FIG. 4, is connected by suitable supply line or tube 16 to a source 18 of thermally controlled air which is schematically illustrated. The term air as used herein is intended to encompass mixtures of gases of controlled composition. The apparatus is constructed to apply a continuous stream of thermally controlled air to a wound treatment volume. While the apparatus was conceived and constructed for applying a heated stream of air, it may also be used to apply a cooled stream of air if required.

The specific form of the apparatus and details of construction can best be understood by reference to the various figures. The overall appearance of the wound covering is best seen in FIG. 4 and FIG. 5. It is preferred to construct the apparatus from top and bottom sheets of thin heat-sealable polymer film which overly one another. A top sheet or membrane 20 overlies a bottom sheet or membrane 22 and they are heat sealed together along a plurality of seal lines, including a continuous outer seam 24, which extends in a circle around the head 12 and continues in a sinusoidal or convoluted fashion along and forming the air tube portion 14. An inner continuous circular seam 26 is provided as best seen in FIG. 6 and in FIG. 7. This inner seam secures the sheets together along a continuous circle to form the inner wall of a torus defining a supply volume 28.

The inner circular portion of the two sheets lying in the plane within the center of the supply volume 28 forms a wall 30 separating a lower wound treatment volume 32, from an upper insulation chamber 34. The wall 30 includes multiple apertures 36 formed by making small circular seals 38 and cutting and removing circular portions within the circular seals 38. Thus, a wall 30 with a plurality of apertures 36 is formed between the wound treatment volume 32 and insulation chamber 34. A plurality of apertures 40 are formed in the common circular wall surrounding the treatment volume 32 for distributing and conveying heated air or gases from the supply volume 28 into the wound treatment volume 32.

The heated air flowing into the treatment volume 32 bathes and contacts the wound surface of a patient's body 42. The air circulates throughout the wound treatment volume 32, and then passes through the apertures 36 into the upper or insulating chamber 34, where it then passes through a circular filter 44 forming an outer wall of the insulation chamber 34. The filter 44 filters the air leaving the wound treatment volume to trap contaminants shed from the wound. The filter 44 may be constructed of a filter paper bonded along its periphery to the outer tangential walls of the housing forming the torus or supply chamber 28. The filter paper also provides an insulating layer which suppresses loss of heat by radiation through the upper wall 30.

The lower surface of the head 12 as shown in FIG. 6 and FIG. 7, is preferably provided with a peripheral sealing ring 46 made of an absorbent material such as foam and bonded by suitable adhesive to the walls of the housing and the skin of the patient around the wound. Preferably, the foam or cotton peripheral sealing ring 46 is provided with a peel-off tape so that it adheres to the wall of the housing and on the other side to the skin of the patient. The adhesive or tape holds the apparatus in place and prevents airflow escape between the device and the skin of the patient. The absorbent material of the ring absorbs weeping blood and fluids and insulates the skin from direct heat in the tube.

The supply hose 14 is designed to be non-kinking by forming it of symmetrically convoluted flexible material. The hose and housing are integrally formed essentially of a unitary structure, such as a thin film membrane. The supply hose section 14 is inflatable upon the application of heated air through the supply line 16. The indentations in the hose section 14 permit it to bend without kinking and, thus, differentiate from a straight tubular hose which may kink when bent.

Since the thermal body treatment apparatus of the invention and the supply hose section are formed from two, thin, sealed-together membranes, the hose, and in fact the entire apparatus, is collapsible. This prevents the possibility of applying heat and pressure to the skin as might happen if a disoriented patient rolled over on the device. Instead, the weight of the patient's body would collapse the device, obstructing the flow of air, and preventing the application of heat.

The film membrane may preferably be transparent. to enable viewing the wound without removal. However for cosmetic reasons the barrier layer may be opaque. The filter paper 44 is attached across the tangential surfaces of the toroidal housing, thus providing a large area of filter for the escaping air. The head of the apparatus may be about one foot in diameter for most applications. However, it may be made smaller for certain other applications.

FIG. 8A illustrates an exploded view of an alternate embodiment of a non-contact wound covering 120 with climate control within the treatment volume 122. An inflatable structure 124 is preferably attached to a fluid inlet line 126 at a fluid inlet port 12 on the perimeter of the inflatable structure 124. The inflatable structure 124 is preferably attached to an absorbent peripheral sealing ring 128, which is in turn attached to the wound area 54 by a suitable adhesive 56. The peripheral sealing ring 128 preferably has a sealed outer surface and a porous inner surface which performs the same function as the peripheral sealing ring 52 discussed above. A barrier layer 130 having an exhaust filter 132 is attached to top surface 134 on the inflatable structure 124.

Turning now to the assembly illustrated in FIG. 8B, a gas illustrated by the arrows A, is introduced into the inflatable structure 124 from an external source (not shown) through the inlet line 126. The gas pressurizes the inflatable structure 124 in order to maintain the barrier layer 130 and exhaust filter 132 in an elevated position relative to the wound area 54. The inner surface 136 of the inflatable structure 124 preferably has a plurality of apertures 138 through which the fluid is introduced into the wound treatment volume 122. As the pressure within the treatment chamber increases, excess pressure is relieved through the exhaust filter 132. In this fashion, various fluids or gases can be introduced into the wound treatment volume 122.

The use of the term "fluid" in the context of this application refers to both liquid and gaseous materials, and combinations thereof. In one embodiment, oxygen may be introduced into the treatment volume 122 through the apertures 138 of the inflatable structure 124. The presence of oxygen within the wound treatment volume 122 may increase the oxygen available to the superficial layer of growing cells in the wound area 54. Nitric oxide may alternatively be infused into the treatment volume 122. Nitric oxide (NO) is a potent vasodilator which in theory may be absorbed across the wound surface and increase localized blood flow. A very small concentration of NO (parts per million) may provide this effect. NO may also be pre-absorbed into the absorbent peripheral sealing ring 128 and then allowed to passively diffuse into the volume once it is applied to the wound. Finally, gaseous or aerosolized medications or compounds may be introduced into the gas flow entering the treatment volume 122.

FIG. 9A and FIG. 9B illustrate an alternate embodiment of the climate control system discussed above wherein a fluid inlet line 140 may form part of a barrier layer 142. The barrier layer 142 is unitary with the fluid inlet line 140 and is preferably attached to an exhaust filter media 144 to allow excess pressure to be released from the wound treatment volume 146. In this embodiment, the filter media 144 forms part of the barrier 142. The arrows "A" in FIG. 9B illustrate the movement of the fluid though the fluid inlet line 140, the treatment volume 146, and the exhaust filter 144.

Figure 10:
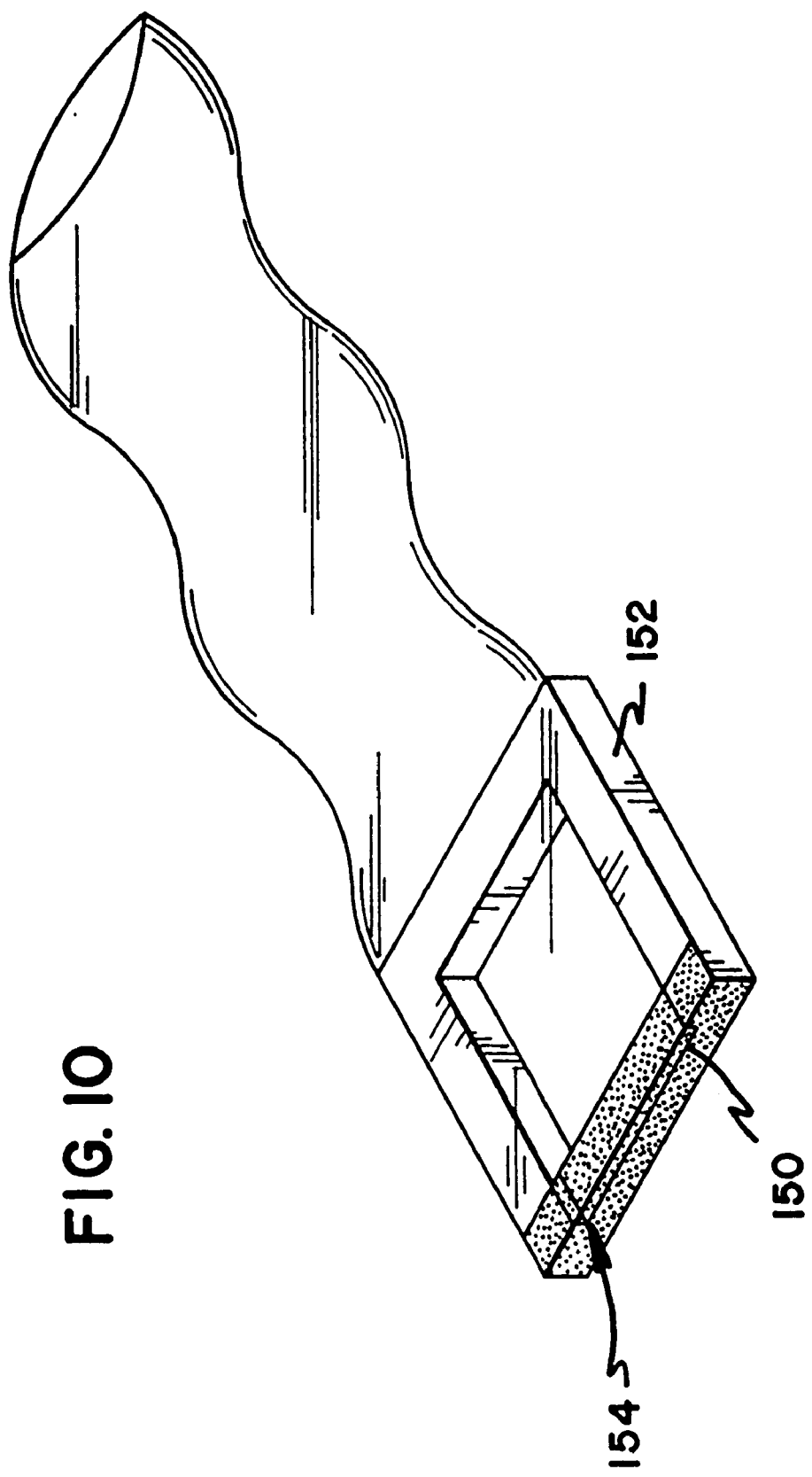
FIG. 10 is a perspective view of an alternate wound covering.

FIG. 10 illustrates an alternate embodiment wherein an exhaust filter 154 is retained in a recess 150 formed in one side of a peripheral sealing ring 152. This structure allows the excess fluid to be exhausted through the side of the peripheral sealing ring 152, rather than through the top, as illustrated in FIG. 9A and 9B.

Figure 11:
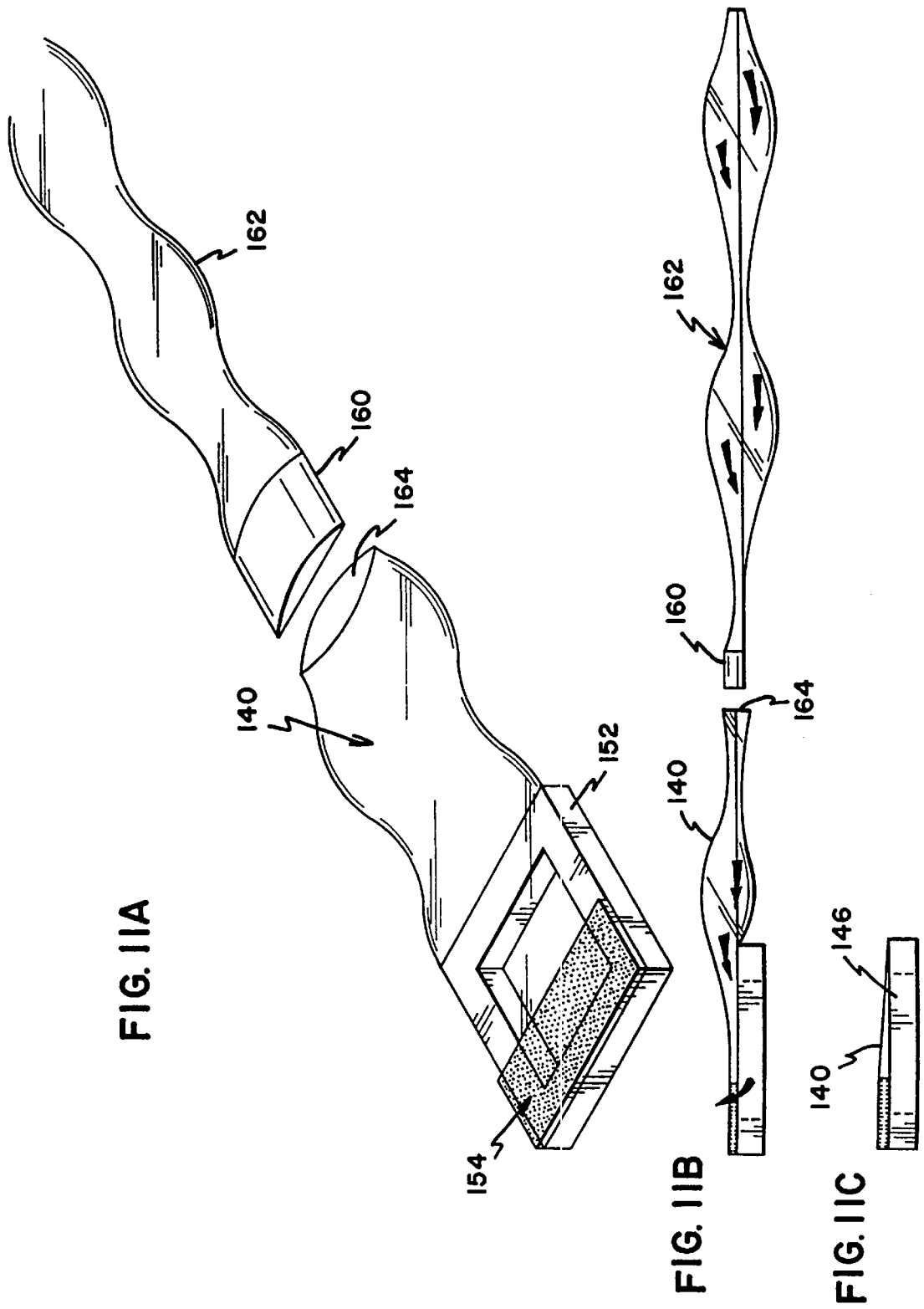
FIG. 11A is a perspective view of an alternate wound covering.
FIG. 11B is a side cross-sectional view of the wound covering of FIG. 11A.
FIG. 11C is a view of the wound covering of FIG. 11A.

FIG. 11A is a perspective view of the embodiment illustrated in FIG. 9A wherein a connector 160 on the end of a fluid supply line 162 engages with an opening 164 on the fluid inlet line 140. FIG. 11B illustrates a side view of the fluid supply line 162 as it engages with the fluid inlet line 140. FIG. 11C illustrates the embodiment of 11A and 11B where the fluid inlet line 140 is folded over the top of the peripheral sealing ring 152 to seal the treatment volume 146 when the supply line 162 is uncoupled.

Figure 12:
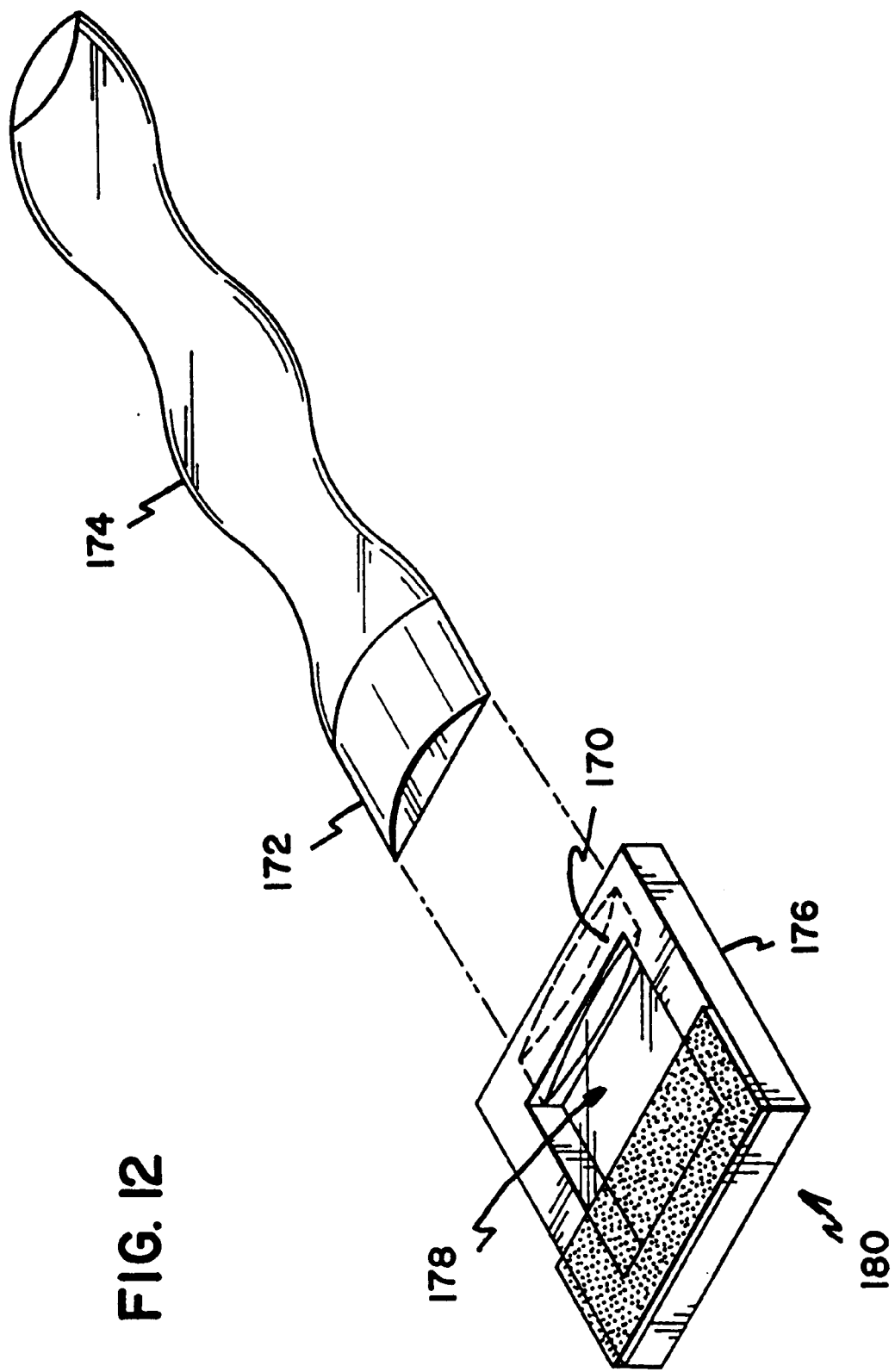
FIG. 12 is a perspective view of an alternate connector apparatus for the wound covering.

FIG. 12 illustrates an alternate embodiment in which a fluid inlet slot 170 engages with a rigid connector 172 on a fluid inlet line 174. The fluid inlet slot 170 forms an opening in one portion of the peripheral sealing ring 176. The opening is in fluid communication with the treatment volume 178. This configuration allows for quick disconnect of the fluid inlet line 174 from the wound covering 180 to provide the patient with additional mobility.

Figure 13:
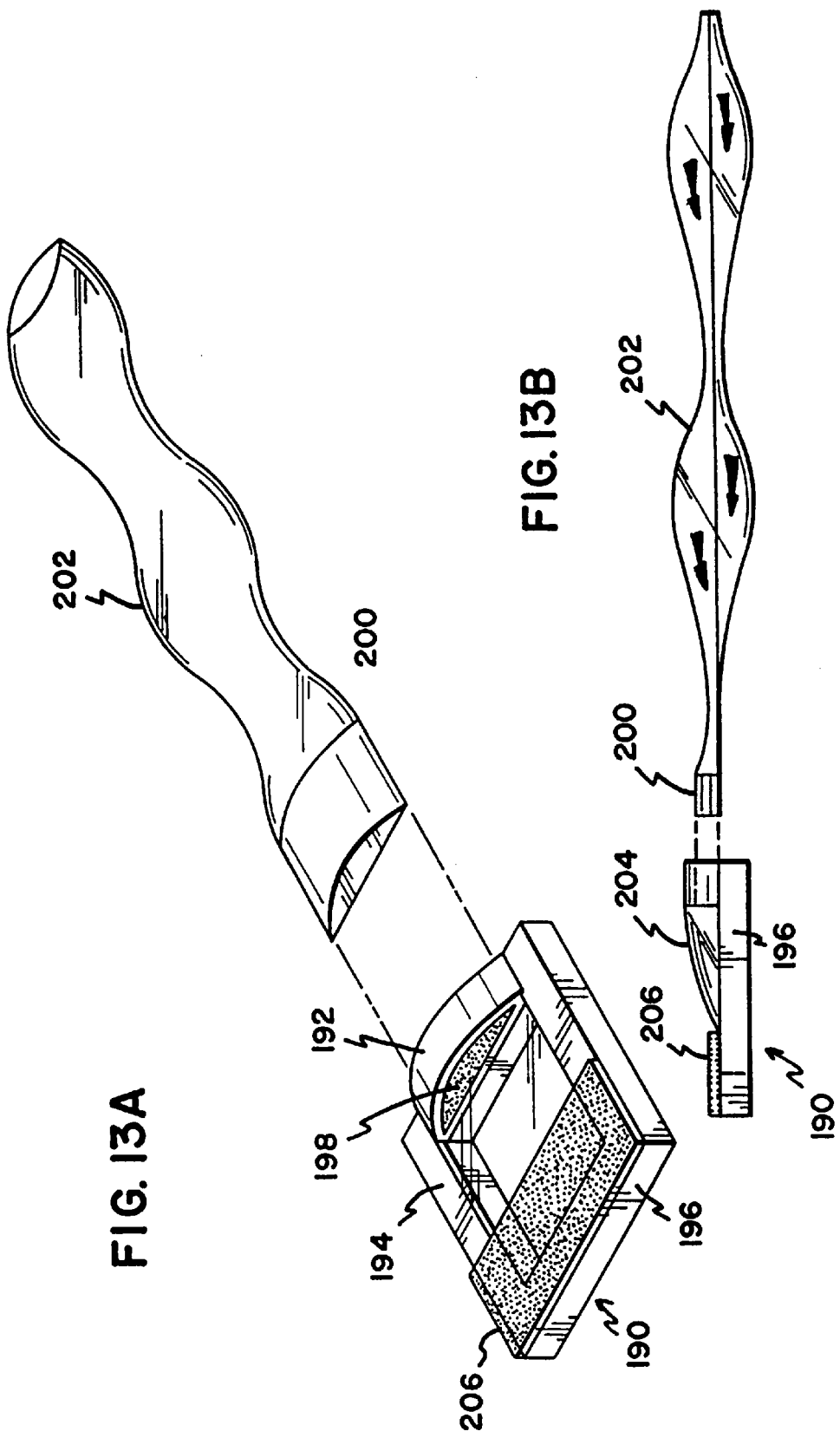
FIG. 13A is an alternate connector arrangement for the wound covering.
FIG. 13B is a side sectional view of the wound covering of 13A.
Figure 14:
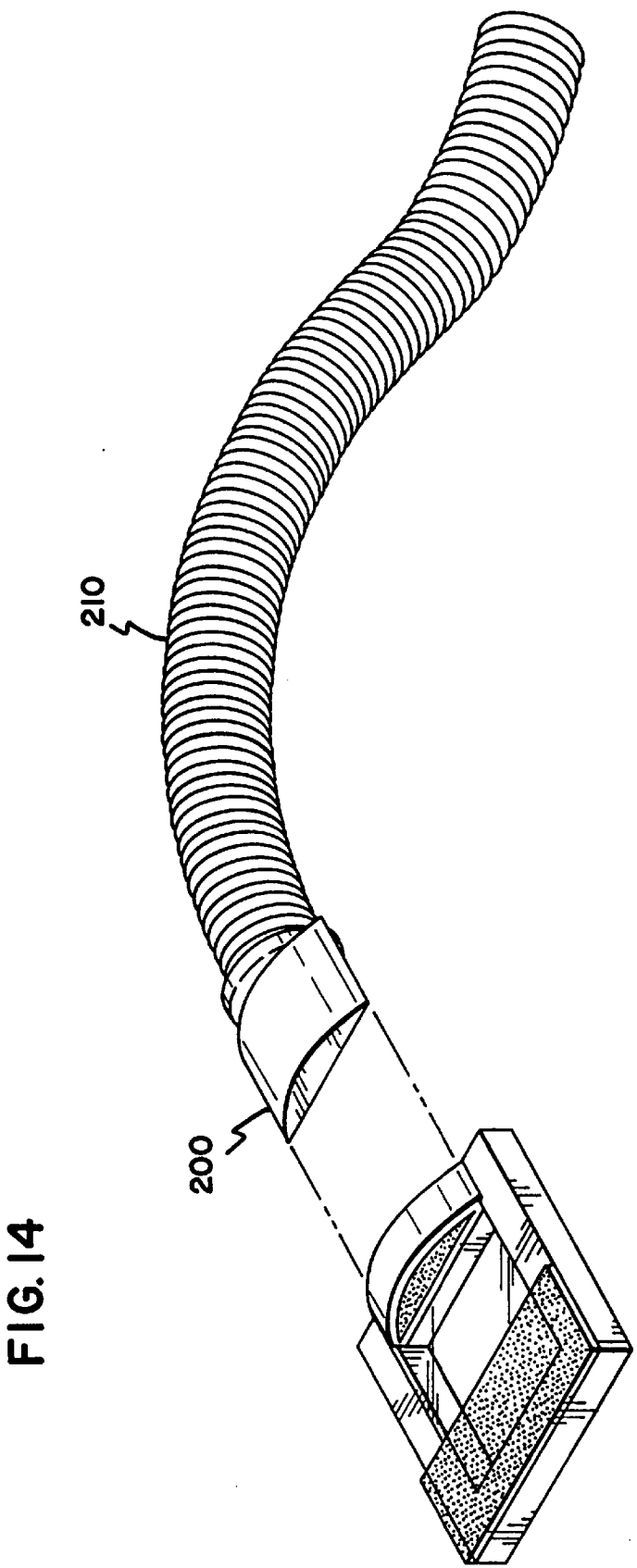
FIG. 14 is a view of a rigid connector for engagement with a wound covering.

FIG. 13A is a perspective view of an alternate non-contact wound covering 190 having a fluid inlet connector 192 attached to a top surface 194 of the peripheral sealing ring 196. The fluid inlet connector 192 preferably contains an inlet filter media 198. A rigid connector 200 on a fluid inlet line 202 mates with the fluid inlet connector 192. As illustrated in FIG. 13B, a cover 204 extends from the top of the fluid inlet connector 192 across the top of the peripheral sealing ring 196 where it engages with an exhaust filter media 206. FIG. 14 illustrates the embodiment of FIGS. 13A and 13B utilizing a non-disposable fluid supply line 210.

Figure 15:
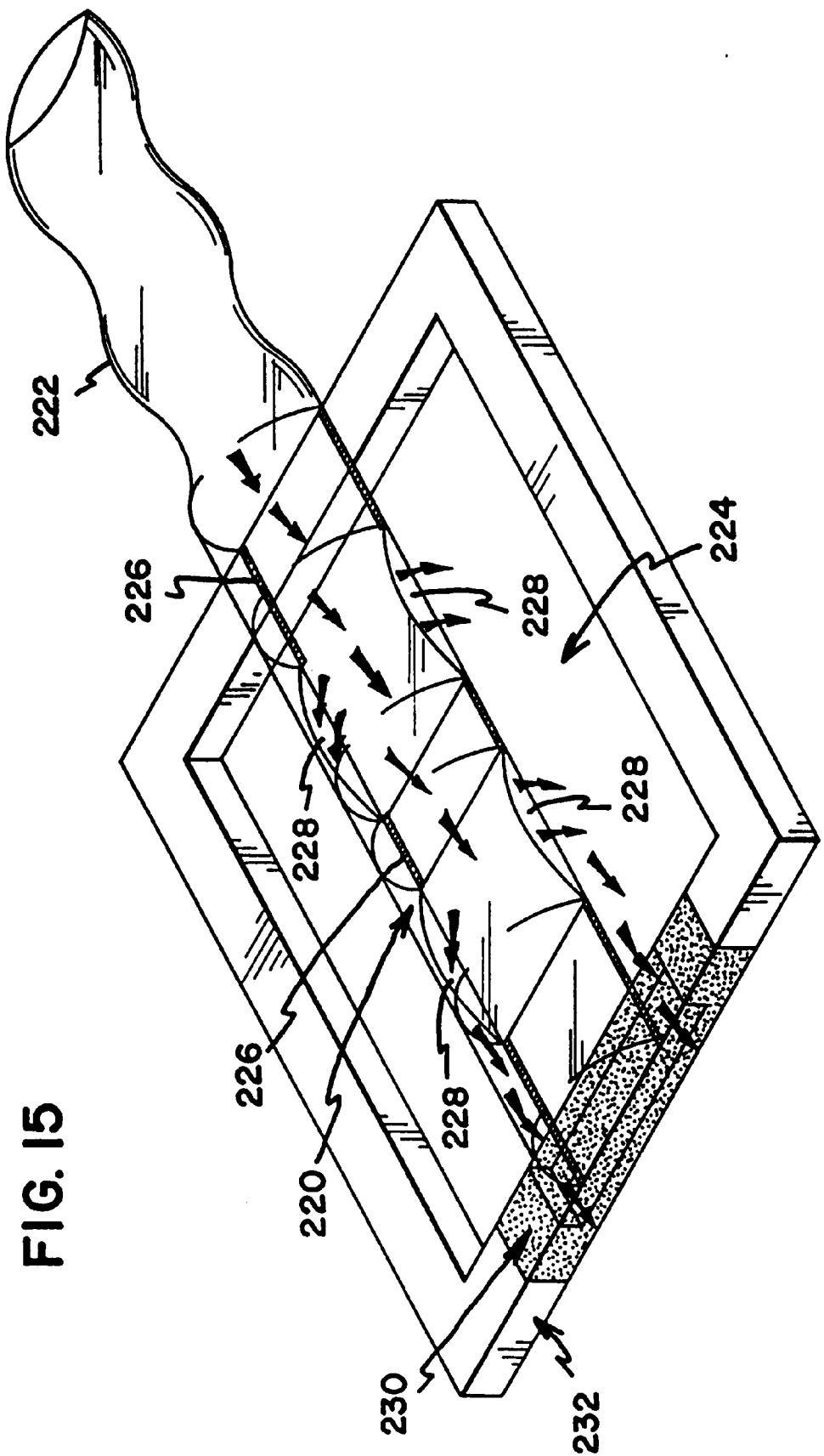
FIG. 15 is an alternate fluid inlet line for the wound covering.

FIG. 15 illustrates an alternate embodiment which utilizes a manifold structure 220 as part of the fluid inlet line 222 to provide even distribution of the fluid being introduced into the treatment volume 224. The fluid inlet line 222 preferably has a series of seals 226 along its edge which are interrupted by a plurality of side openings 228 from which the fluid can be transmitted into the treatment volume 224. The embodiment disclosed in FIG. 15 illustrates an exhaust filter 230 recessed into the side of the peripheral sealing ring 232. However, it will be understood that a variety of exhaust filter configurations are possible with the disclosed manifold structure 220.

Figure 16A:
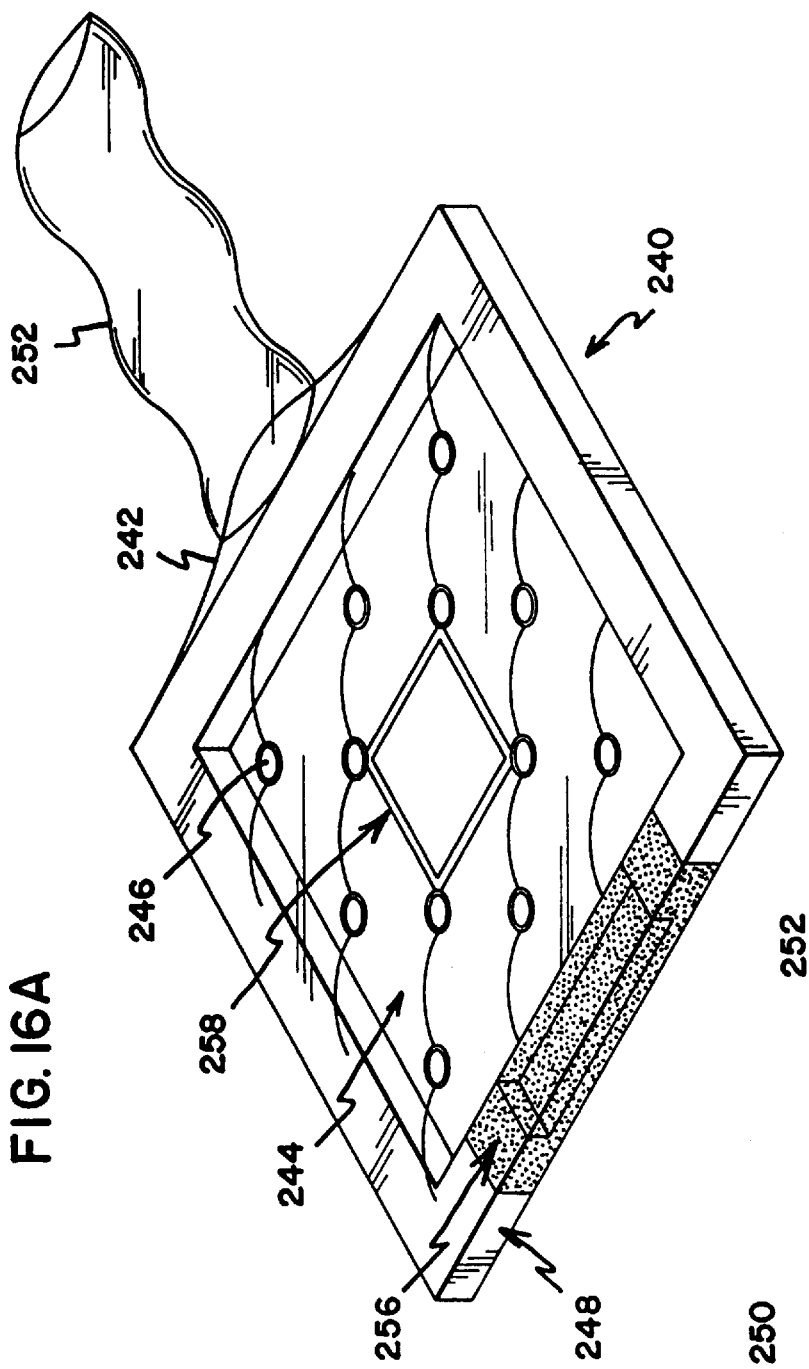
FIG. 16A is a view of a two ply barrier layer wound covering.
Figure 16B:
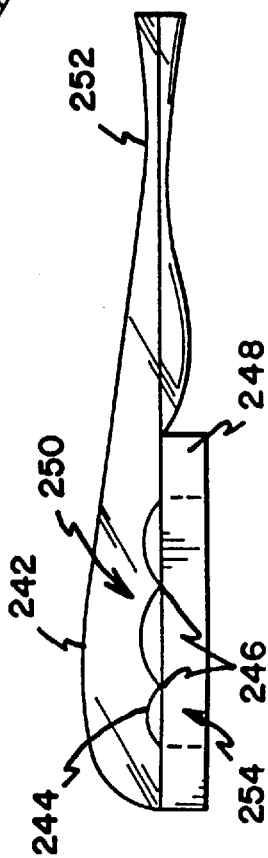
FIG. 16B is a cross-sectional view of the wound covering of 16A.

FIGS. 16A and 16B illustrate an alternate wound covering 240 with a top barrier layer 242 and a lower layer 244 having a plurality of holes 246. As is illustrated in FIG. 16B, the top cover forms the barrier layer 242 and it extends substantially across the area of the peripheral sealing ring 248. The lower layer 244 likewise extends across the peripheral sealing ring 248. An upper insulating layer 250 is formed between the lower layer 244 and the top of the barrier layer 242. Fluid in the fluid inlet line 252 is directed into the upper insulating layer 250. The pressurized fluid in the upper insulating layer 250 passes through the holes 246 into the treatment volume 254. The holes 246 in the lower layer 244 provide generally even distribution of the fluid within the wound treatment volume 254. An optional seal 258 may be formed in the center portion of the barrier layer 242 and the lower layer 244 to provide the layers with additional structural support. An exhaust filter medium 256 is provided in a recess along one side of the peripheral sealing ring 248 to relieve pressure in the treatment volume 254.

FIG. 17 illustrates an alternate embodiment of a non-contact wound covering 260 utilizing semi-rigid supports 262 to retain the barrier layer 264 above the wound area. It will be understood by those skilled in the art that a variety of semi-rigid supports 262 may be utilized for this application. For example, plastic or resilient rubber materials may provide sufficient support to the barrier layer 264 with a minimum risk of injuring the patient.

FIG. 18A and FIG. 18B illustrate an alternate exhaust filter medium 270 with an enlarged surface area to accommodate larger volumes of air flow through the non-contact wound covering 280. The exhaust filter is incorporated into the fluid inlet line 272. The fluid inlet line 272 also forms a portion of the barrier layer 274, which is in turn attached to the peripheral sealing ring 276. As is best shown in FIG. 18B, fluid illustrated as the arrows "A" is introduced into the fluid inlet line 272, where it is directed into the wound treatment volume 278, past the wound area and out through the exhaust filter medium 270.

Figure 19:
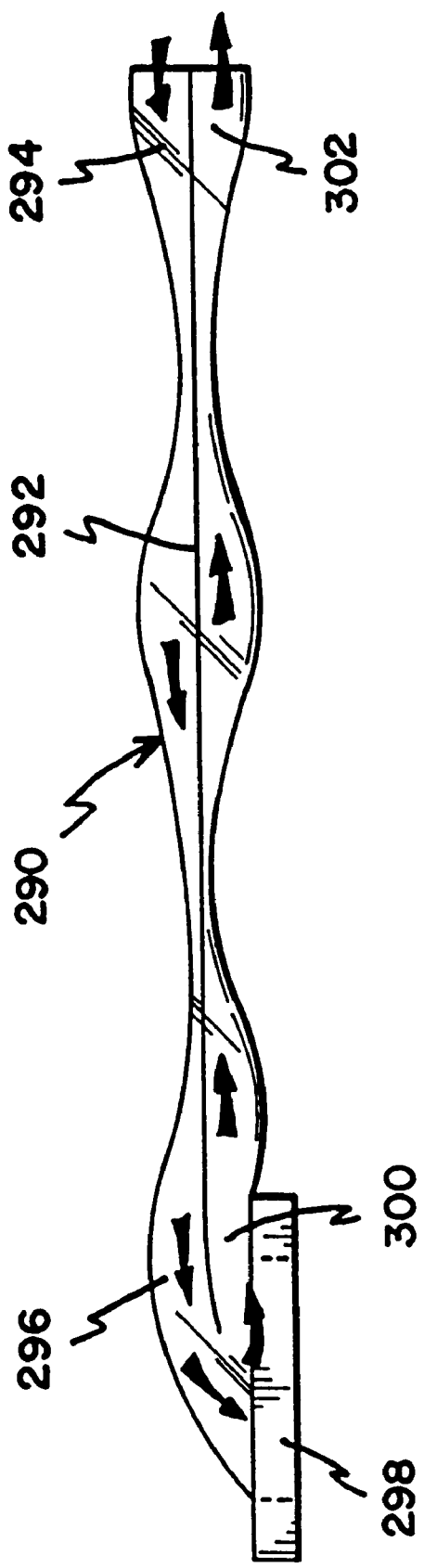
FIG. 19 is a view of an alternate wound covering.

FIG. 19 illustrates a bi-directional line 290 with a center divider 292. Fluid is introduced into the fluid inlet line 294 where it proceeds through a fluid inlet port 296 into the treatment volume 298. The fluid then is forced through a fluid outlet port 300 where it is driven away from the treatment volume 298 in a fluid outlet line 302. It will be understood by those skilled in the art that it would be possible to utilize separate fluid inlet and outlet lines to achieve the same result.

While the invention has been illustrated by means of specific embodiments, it will be evident to those skilled in the art that many variations and modifications may be made therein. However, it is to be understood that the scope of the present invention is to be limited only by the appended claims.

What is claimed:

1. A wound covering for application to a wound area of a patient's body, the wound covering comprising:

a sealing ring, having an upper surface and a lower surface, defining an open cavity for placement over and sealing around the wound area;

a barrier layer spanning the sealing ring and attached to the sealing ring proximate the upper surface and spaced apart from the selected wound area by the sealing ring;

the barrier layer comprising a gas permeable film;

the sealing ring for supporting the barrier layer above the level of the wound area;

the sealing ring and the barrier layer together defining a wound treatment volume;

wound area attachment means, proximate the second lower surface, for permitting attachment of the sealing ring to the wound area; and means proximate the barrier layer for retaining a heater above the level of the wound area.

2. The wound covering of claim 1 in which the sealing ring comprises a conformal polymeric foam ring.

3. The wound covering of claim 1 further comprising a heater, retained over the barrier layer by the means, for heating the treatment volume and selected wound area.

4. The wound covering of claim 3 in which the heater comprises an active heater.

5. The wound covering of claim 4 further comprising a switch to turn off the active heater.

6. The wound covering of claim 4 further comprising a thermostat coupled to the active heater to regulate the temperature of the treatment volume.

7. The wound covering of claim 3 in which the heater comprises a passive heat reflecting layer.

8. The wound covering of claim 1 in which the means comprises a pocket adapted for receiving the heater.

9. The wound covering of claim 1 in which the wound area attachment means includes an adhesive applied to the lower surface and a release liner releasably attached to the adhesive.

* * * * *

UNITED STATES PATENT AND TRADEMARK OFFICE
CERTIFICATE OF CORRECTION

PATENT NO. : 5,961,480  
DATED : October 5, 1999  
INVENTOR(S) : Scott Augustine It is certified that error appears in the above-identified patent and that said Letters Patent is hereby corrected as shown below:

<u>Title page,</u>
Item [62], please add after "Dec. 29, 1997" -- , now U.S. Patent No. 5,947,914, which issued September 7, 1999, which is a continuation application of U.S. Patent Application Serial No. 08/356,325, filed February 21, 1995, now abandoned, which is a 35 U.S.C. § 371 application of PCT international application Serial No. PCT/US93/05876, filed June 18, 1993, which is a continuation-in-part of, and claims priority from, U.S. Patent Application Serial No. 07/900,656, filed June 19, 1992, now abandoned --.

<u>Column 1,</u>
Line 3, please add after "Dec. 29, 1997" -- , now U.S. Patent No. 5,947,914, which issued September 7, 1999, which is a continuation application of U.S. Patent Application Serial No. 08/356,325, filed February 21, 1995, now abandoned, which is a 35 U.S.C. § 371 application of PCT international application Serial No. PCT/US93/05876, filed June 18, 1993, which is a continuation-in-part of, and claims priority from, U.S. Patent Application Serial No. 07/900,656, filed June 19, 1992, now abandoned --.

Signed and Sealed this

Twenty-eighth Day of January, 2003

JAMES E. ROGAN  
*Director of the United States Patent and Trademark Office*